United States Patent
Lara

[19]
[11] Patent Number: 6,111,243
[45] Date of Patent: Aug. 29, 2000

[54] MULTI-AXIS PHOTOMETRIC INSPECTION SYSTEM AND METHOD FOR FLAT PANEL DISPLAYS

[75] Inventor: Hector Lara, Los Angeles, Calif.

[73] Assignee: Photo Research, Inc., Chatsworth, Calif.

[21] Appl. No.: 09/016,010

[22] Filed: Jan. 30, 1998

[51] Int. Cl.[7] .................................................. H01L 27/00
[52] U.S. Cl. ...................... 250/208.1; 348/191; 356/218
[58] Field of Search ............................... 250/548, 208.1; 356/218, 219, 222; 348/189, 191

[56] References Cited

U.S. PATENT DOCUMENTS

| | | | |
|---|---|---|---|
| 4,279,507 | 7/1981 | Bulpitt | 356/225 |
| 4,554,460 | 11/1985 | Klein | 250/578 |
| 4,593,368 | 6/1986 | Fridge et al. | 364/525 |
| 4,648,053 | 3/1987 | Fridge | 364/551 |
| 4,893,925 | 1/1990 | Sweeney et al. | 356/72 |
| 4,917,488 | 4/1990 | Glass | 348/191 |
| 5,028,134 | 7/1991 | Bulpitt et al. | 356/328 |
| 5,267,038 | 11/1993 | Fister | 358/139 |
| 5,440,340 | 8/1995 | Tsurutani et al. | 348/191 |
| 5,796,425 | 8/1998 | Minami et al. | 348/189 |

*Primary Examiner*—Stephone Allen
*Attorney, Agent, or Firm*—Darby & Darby

[57] ABSTRACT

A system and method for inspecting an image-producing display according to a predetermined footprint is disclosed. The system includes a platform fixed to a first multi-axis positioning unit for supporting the display. A sensing head is disposed in confronting relationship with the platform to detect light produced by the display. The sensing head is carried by a second multi-axis positioning unit. The system also includes a controller having outputs coupled to the respective first and second positioners. The controller is operative to generate control signals for manipulating the respective positioners and arranging the display and the sensing head into one or more relative orientations defining the inspection footprint.

16 Claims, 6 Drawing Sheets

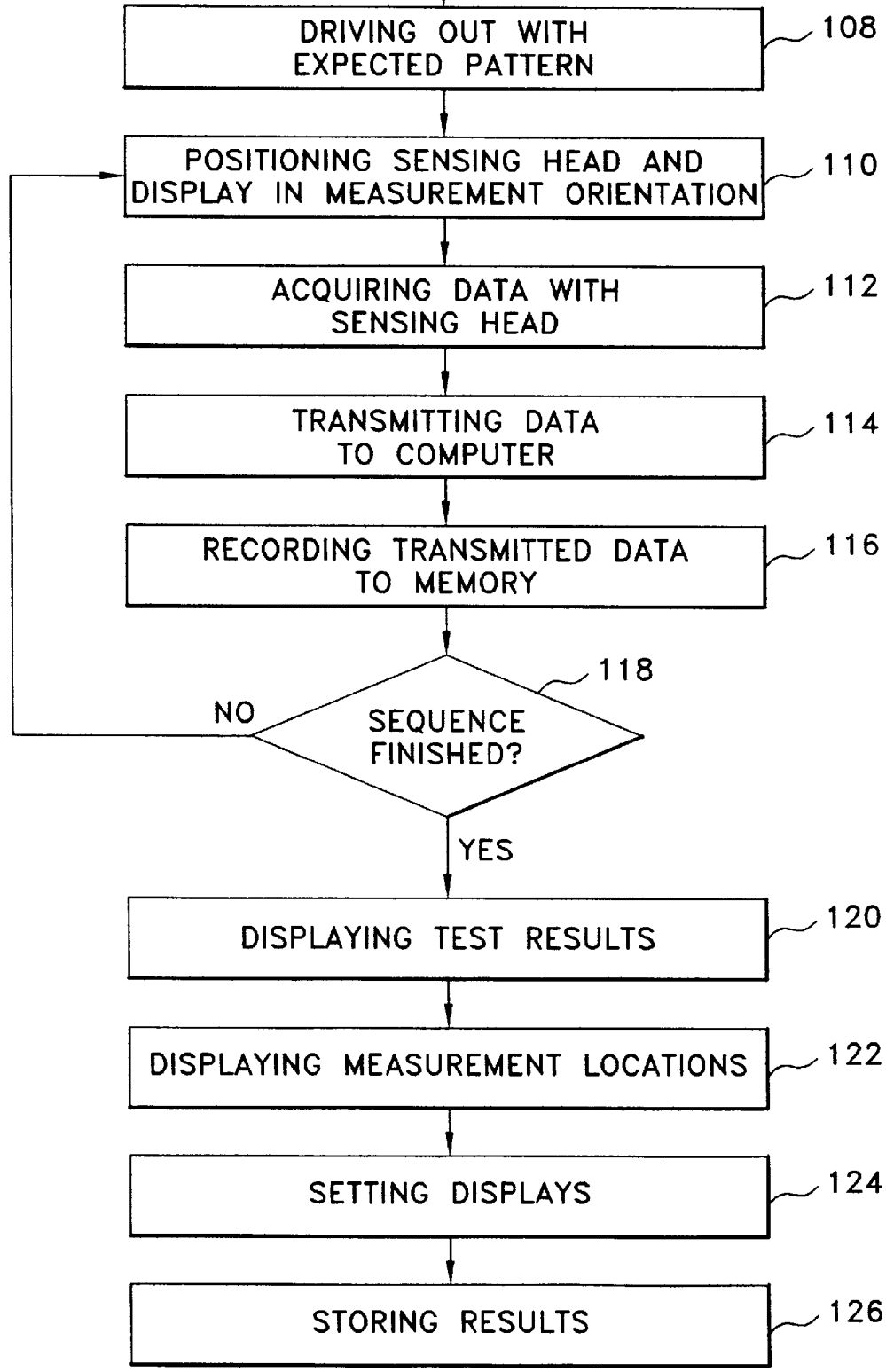

MULTI-AXIS PHOTOMETRIC INSPECTION SYSTEM AND METHOD FOR FLAT PANEL DISPLAYS

FIELD OF THE INVENTION

The invention relates to the manufacture and testing of image producing displays, and more particularly to a multi-axis inspection system and method for measuring and analyzing the properties of radiation emitted from flat panel displays.

BACKGROUND OF THE INVENTION

Flat panel displays, or FPD's, are becoming increasingly more popular as an alternative to monitors utilizing conventional cathode ray tube (CRT) technology. FPD's, such as liquid crystal or active matrix displays, have inherent compactness advantages over CRT's because of their electronic nature. This advantage is readily apparent when noting the relative sizes between a personal computer monitor and a laptop computer display screen.

To satisfy the increasing demand for FPD's, manufacturers have sought to improve manufacturing efficiencies in production and, most notably, in the quality control area. Quality control often refers to the inspection, testing, or verification of one or more parameters of a device. Of significant importance for quality control purposes relating to FPD's are accurate measurements of the photometric and colorimetric properties of light generated by the displays under test. One of the keys to verifying the operability of FPD's is to employ instruments capable of detecting emitted radiation that corresponds as closely as possible with what an average human observer would experience.

Initial attempts at inspecting FPD's utilized conventional CRT inspection and measurement systems. Typically, these systems employed a photometer disposed in confronting relationship to the CRT for detecting one or more parameters of the light emitted by the display, such as luminance, contrast and chromaticity. To position the photometer at different orientations relative to the display, the system included a three-axis table having respective stages moveable along a Cartesian coordinate system. During test, the display remained fixed in an immobile position as the instrumentation followed an inspection path, or footprint.

While the conventional CRT inspection system described above worked well for its originally intended uses, as flat panel display technology improved, those skilled in the art recognized that measurements of the displays at orientations not normal to the display surface were not being considered in the verification criteria. This is primarily explainable because of the physics involved in the operation of CRT's which allows viewing of the screen from an angle with little effects on the light intensity sensed from particular pixels. Unlike CRT's, visible radiation emitted from FPD's drops off in intensity when viewed from the side, or at angles to the flat surface. This is because FPD's employ polarizing optics that cause the visible radiation emitted to drop off in intensity when viewed from the side, or at angles to the flat panel surface.

To account for angular flat panel display measurements, those skilled in the art proposed a relatively large and cumbersome five-axis inspection system. This system included the features of the three-axis CRT inspection system, but employed two additional rotary axes to pivot the instrumentation about two additional axes. With the rotational capability, the inspection equipment could orient the photometer in angular relationship to the display.

While the conventional five-axis system is believed capable of delivering inspection results at fairly acceptable rates of speed, the cumbersome construction of the system is believed capable of significant improvement. The conventional system described above typically has problems testing a range of FPD sizes due to the limited flexibility of the 5-axis positioning mechanism. For FPD testing, it is often important to have the capability of varying the distance between the instrumentation and the DUT quickly. Moreover, thorough FPD testing often involves exposing the DUT to a variety of environmental conditions in a sealed chamber. Conventional systems lack these capabilities.

Thus, the need exists for a multi-axis flat panel display system and method capable of providing measurements at relatively high throughput rates while maintaining a high level of flexibility. Moreover, the need exists for an inspection system having a unique footprint to allow open architectures for integrating into a variety of testing environments. The system and method of the present invention satisfy these needs.

SUMMARY OF THE INVENTION

The multi-axis inspection system and method of the present invention provide a flexible and configurable footprint for testing image producing displays such as flat panel constructions. Because of the footprint flexibility, open architectures are achievable as well as an increased range of measurement capabilities for DUT's of varying sizes.

To realize the advantages above, in one form, the invention comprises a system and method for inspecting an image-producing display according to a predetermined footprint. The system includes a platform fixed to a first multi-axis positioning unit for supporting the display. A sensing head is disposed in confronting relationship with the platform to detect light produced by the display. The sensing head is carried by a second multi-axis positioning unit. The system also includes a controller having outputs coupled to the respective first and second positioners. The controller is operative to generate control signals for manipulating the respective positioners and arranging the display and the sensing head into one or more relative orientations defining the inspection footprint.

In another form, the invention comprises a method of inspecting an image-producing display. The method includes the steps of mounting the display on a first multi-axis positioning unit; selecting a sensing head for measuring light generated by the display, the sensing head being carried by a second multi-axis positioning unit disposed in confronting relationship with the display; defining a footprint comprising a plurality of measurement orientations along a predetermined path; and manipulating the respective first and second positioning units according to the defined footprint to cooperatively bring the display and sensing head into the plurality of measurement orientations and minimize positional accuracy therebetween.

BRIEF DESCRIPTION OF THE DRAWINGS

Other features and advantages of the present invention will be apparent from the following detailed description when read in conjunction with the accompanying drawings, wherein:

FIG. 5 is a flowchart of additional steps employed in the method of FIGS. 4A and 4B.

DETAILED DESCRIPTION OF THE INVENTION

Manufacturing operations often rely heavily on reliable quality control procedures and techniques to verify that finished products operate as expected. In the fabrication of flat panel displays, the verification of various light parameters indicative of the quality of the display is critical to minimize production costs and maintain a competitive product line. The inspection of flat panel displays seeks to acquire and sense emitted radiation in a manner that corresponds as closely as possible with what an average human observer would experience.

Figure 1:
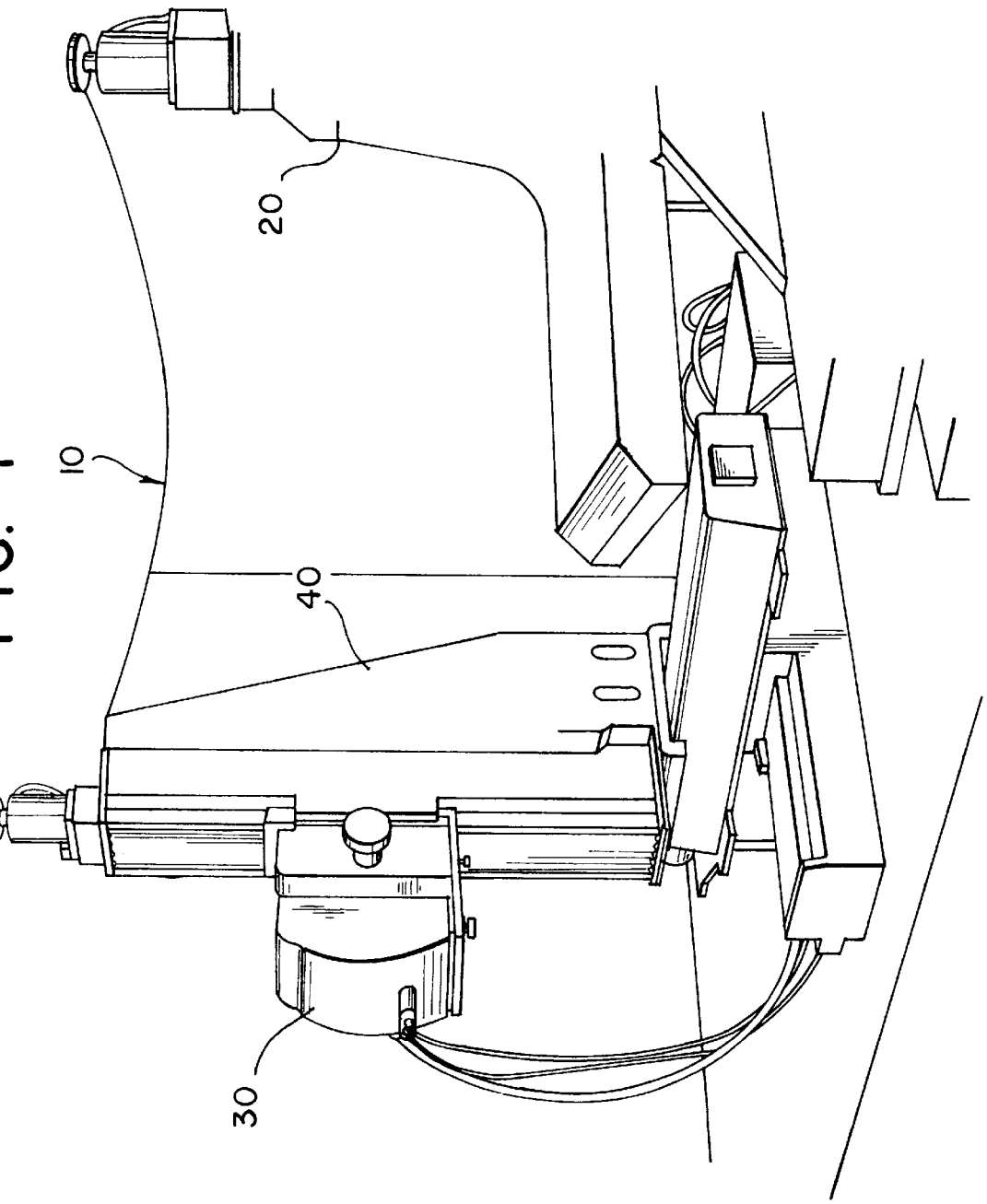
FIG. 1 is a perspective view of the system of the present invention according to one embodiment.
Figure 2:
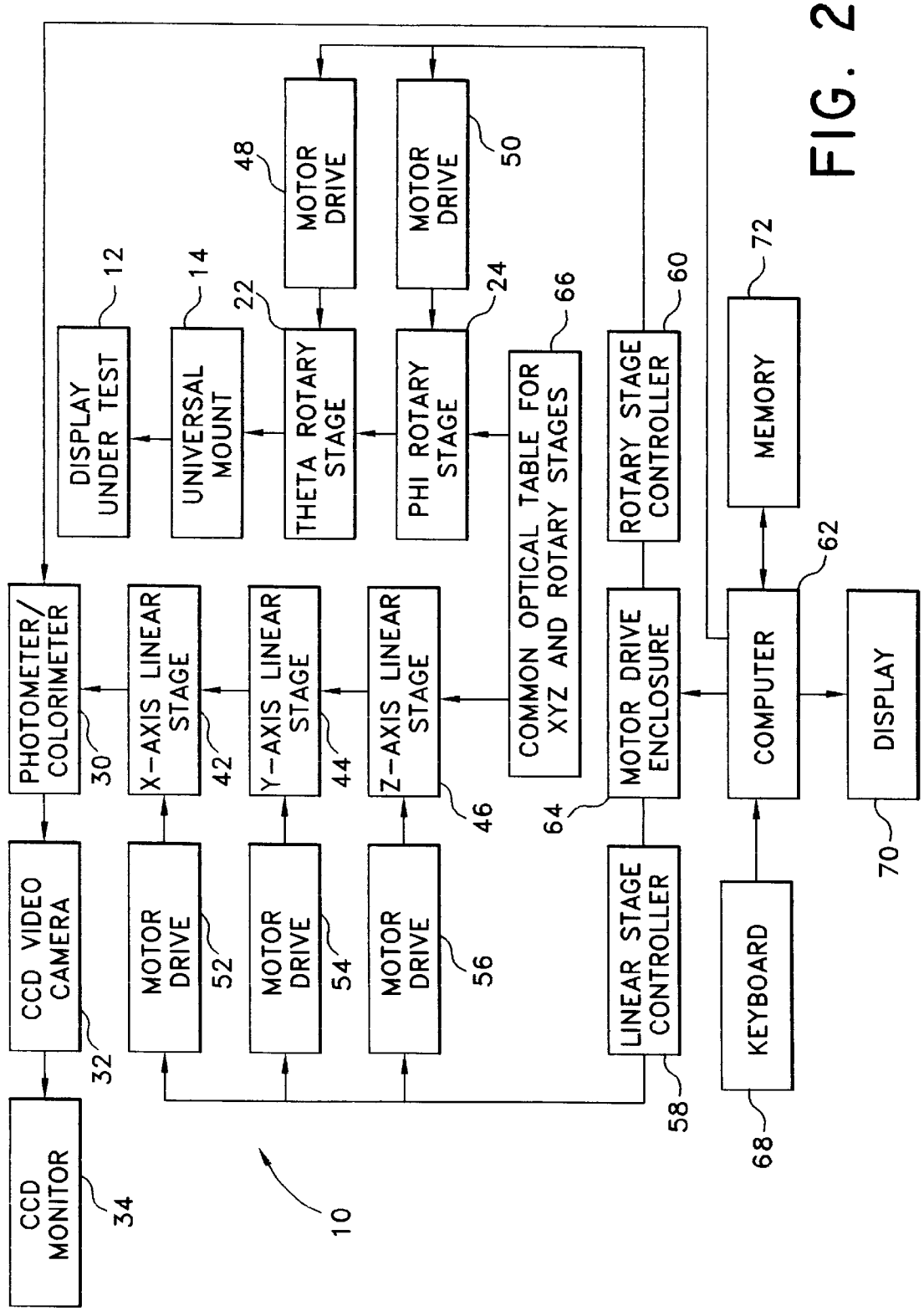
FIG. 2 is a block diagram of the system shown in FIG. 1.

Referring now to FIGS. 1 and 2, the system of the present invention, generally designated 10, measures and analyzes radiation emitted from a display under test (DUT) 12 with a sensing head 30. Respective first and second multi-axis positioning units 20 and 40 cooperate to orient the sensing head and DUT according to a testing sequence that defines an advantageously flexible footprint.

Figure 3:
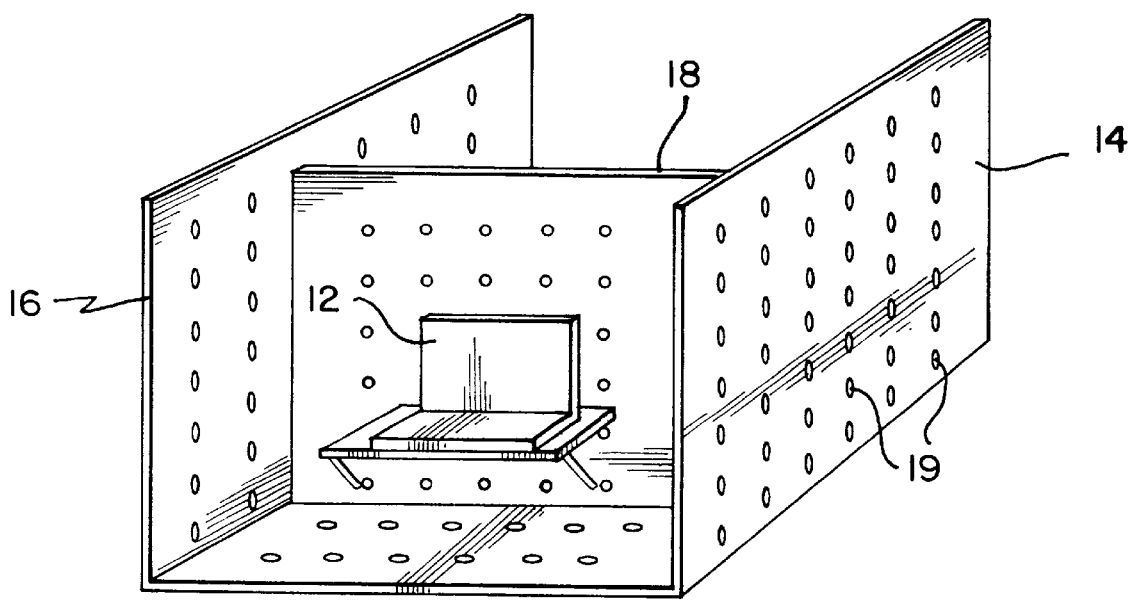
FIG. 3 is a perspective view of the universal mount shown in FIG. 2.

Referring now to FIG. 3, the DUT 12 is supported by a universal mount 14 having the capability of supporting a variety of display sizes. The mount comprises an open box-shaped bracket 16 with a movable face panel 18. The bracket and panel are formed with a plurality of spaced apart breadboard holes 19 adapted for receiving a plurality of fasteners (not shown) to mount the DUT to the panel at variable depths with respect to the sensing head 30. The breadboard configuration allows installation of a range of DUT sizes without the need for customized fixturing and contributes to the overall open architecture capability of the present invention.

Referring again to FIGS. 1 and 2, the universal mount 14 rests upon a dual-axis rotary positioning unit 20 having respective theta and phi stages 22 and 24. The unit is constructed in a North polar goniometer configuration and provides ninety-degrees of rotational movement for each axis within 0.010 degrees of accuracy. A preferred goniometer is available from Daedal Corp., Model No. 081-5081.

With continuing reference to FIGS. 1 and 2, the sensing head 30 is carried by the second multi-axis positioning unit 40 and disposed in confronting relation to the DUT 12. The sensing head comprises one or more light measuring instruments such as a photometer, colorimeter, or both. Preferably, the sensing head includes a filter photometer such as the Pritchard PR-880, and a spectroradiometer such as the PR-650, both available from Photo Research, Inc., of Chatsworth, Calif. Generally, the filter photometer provides high sensitivity for low level intensity measurements while the spectroradiometer contributes greater color detection accuracy.

As an aid in targeting the sensing head 30 on the DUT 12, a CCD video camera 32 is mounted to a viewing eyepiece (not shown) coupled to the sensing head. The camera is coupled to a CCD video monitor 34 for providing real-time positional feedback to a user. This feature is especially useful during homing configurations for the respective positioning units as will be described below.

Further referring to FIGS. 1 and 2, the second multi-axis positioning unit 40 comprises a tri-stage motion base moveable along a Cartesian coordinate system. The base includes respective x, y, and z linear stages 42, 44, and 46 that provide approximately twenty-four inches of travel along each axis and are capable of supporting loads of approximately forty pounds. A preferred motion base is available from Daedal, Model No. 081-5181, X-X'-Y-Z 506ET.

The respective positioning units 20 and 40 are driven by a plurality of servos 48, 50, 52, 54, and 56. The servos comprise precision microstepping motor drivers responsive to commands from respective controllers or indexers 58 and 60 corresponding to the respective positioning units 20 and 40. The controllers, in turn, operate in accordance with software-driven commands issued from a computer 62. A motor drive enclosure 64 houses the respective controllers and the associated electronics. To maintain a horizontal level surface for the respective positioning units, the entire system 10 is supported on a level optical table 66.

With continuing reference to FIGS. 1 and 2, the computer 62 integrates the aforedescribed hardware into a cohesive system and includes a microprocessor such as an Intel Pentium Pro supported by a plurality of peripheral devices such as a user keyboard 68, a display monitor 70, a mass memory 72 of at least two gigabytes, and RAM memory (not shown) of at least 32 megabytes. Software programmed on a Windows NT based platform and stored in the mass memory provides a visually appealing user interface (not shown) for guiding a user through operation of the system 10 according to steps described more fully below that define the method of the present invention. The computer also includes control outputs connected to the respective controllers 58 and 60 and the sensing head 30, and a data input coupled to the sensing head for receiving measurement data.

The system of the present invention 10 is uniquely tailored for high production flat panel display manufacturing environments. This is because of the flexible nature of the modular components and its open-architecture capability. An exemplary application for the system is for the final certification and verification of the radiation emitted by finished flat panel displays.

Figure 4A:
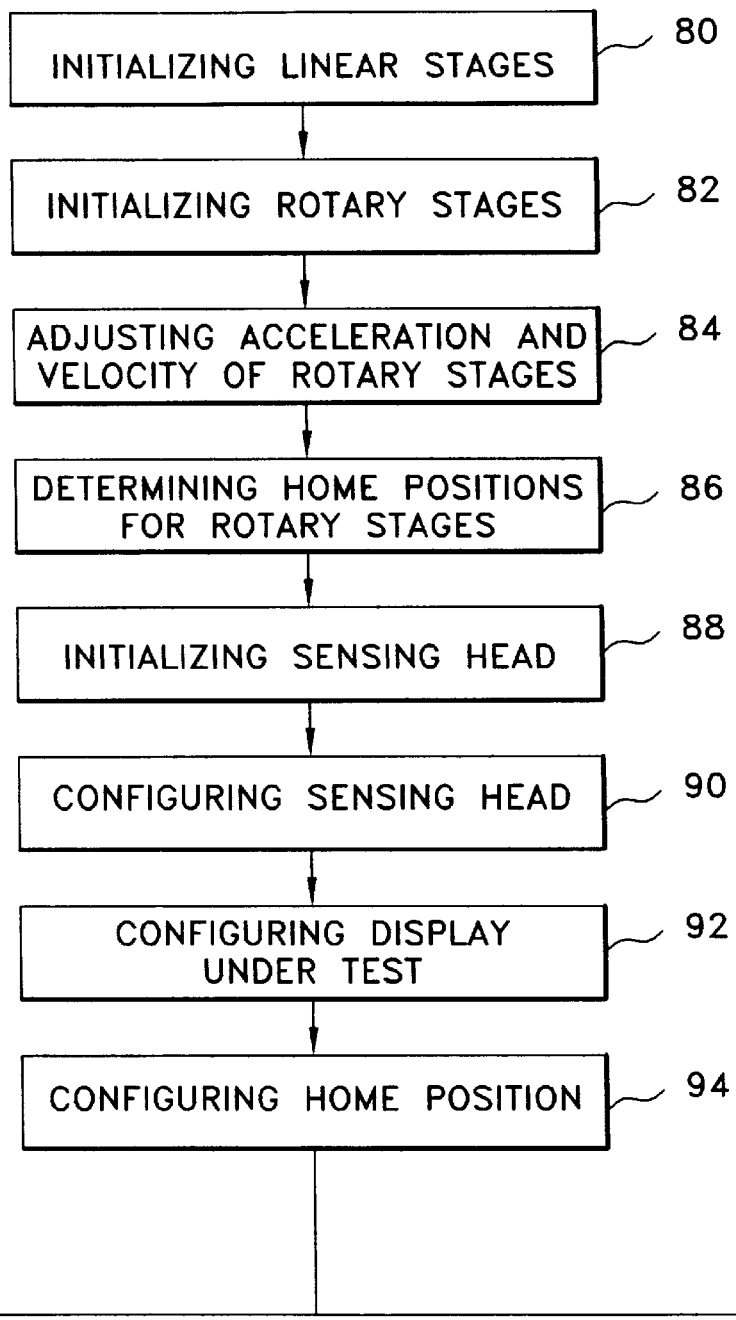
FIGS. 4A and 4B are flowchart of steps according to one embodiment of the present invention.
Figure 4B:
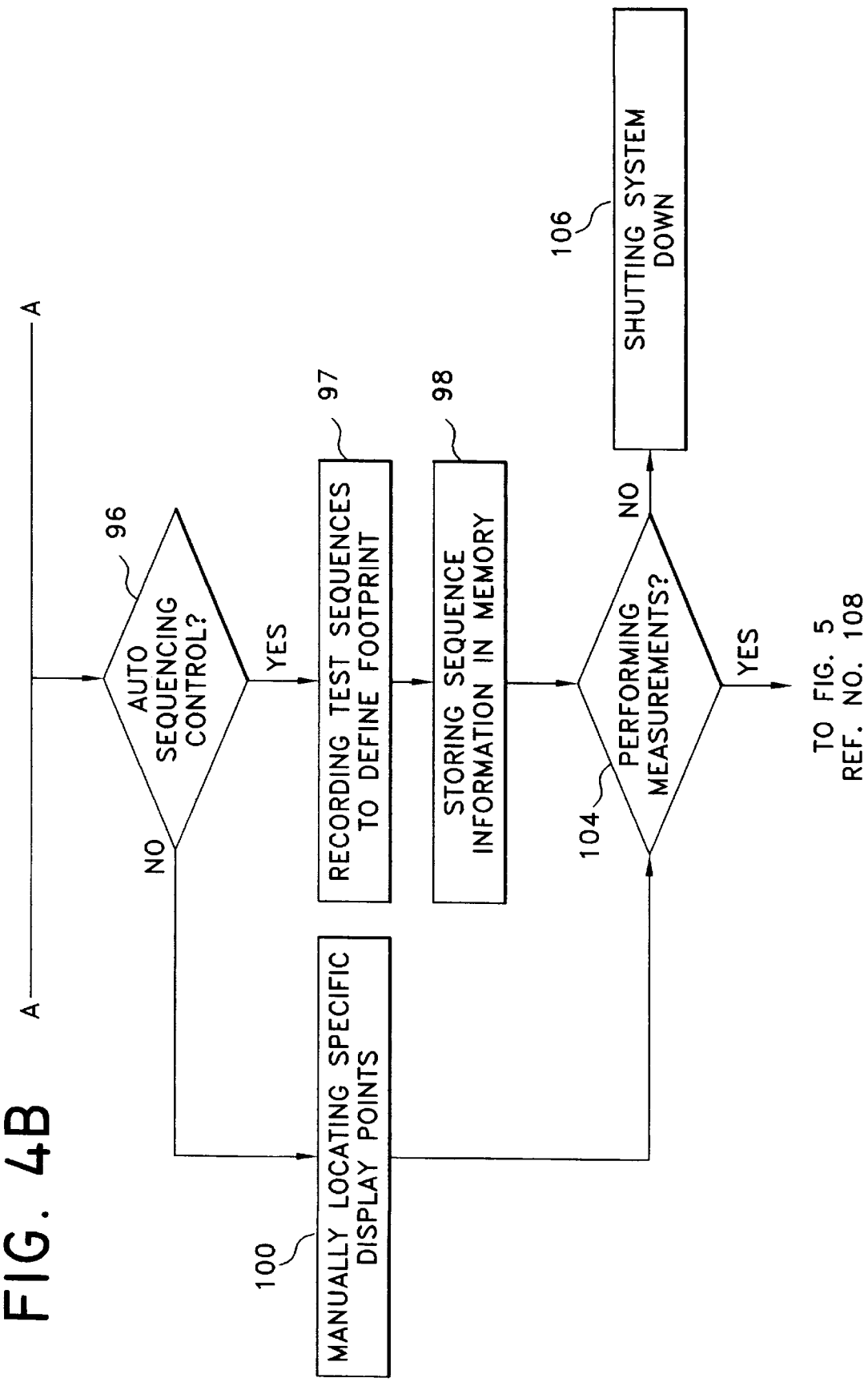

System operation for final test and inspection proceeds according to steps that define the method of the present invention. Referring now to FIGS. 4A and 4B, the system software is first initiated by an operator in order to initialize the linear stages 42, 44, and 46, and the rotary stages 22 and 24 at steps 80 and 82. The software then permits the operator or inspector to adjust the acceleration and velocity of the respective theta and phi rotary stages in both the clockwise and counterclockwise directions, at step 84. It is anticipated that for high production assembly lines, many of the detailed adjustment options will have already been determined and fixed to provide a truly automated testing environment.

Following the adjustment option, the respective home positions for the respective theta and phi stages are manually determined, at step 86. The home position generally represents the "zero" or reference point for positional indication along each axis. The home positions for the linear stages are conveniently defined automatically by the software.

Once the linear and rotary stages are initialized and homed, the software initializes the sensing head 30, at step 88. The software then offers a configuration menu to the user including various parameter setup options for the instrumentation, at step 90. The options include, for example, confirmation information on the actual measurements desired such as luminance, chromaticity, contrast, correlated color temperature, and a variety of other detection parameters. At this time, the DUT 12 is configured, at step 92, by driving the display with video signals defining one or more predetermined visual patterns for emitting expected radiation for detection by the sensing head. Additionally, the home position for the DUT is determined, at step 94.

Following configuration of the sensing head 30 and the DUT 12, the software prompts the user whether to initiate automatic sequencing control, at step 96. If automatic control is selected, the software displays a menu to allow the user to pre-select a plurality of measurement positions or orientations between the sensing head and the DUT. The user then defines the respective stage offsets from the respective home positions for the five axes that correlate to each measurement location. Each measurement definition or selection is then stored to memory, at step 98, as part of an overall test sequence. If automatic control is not selected, then the system software initiates manual mode which involves manually locating specific display points, at step 100.

After the initiation of automatic or manual mode, the user is then prompted to perform measurements on the DUT 12, at step 104. If no measurements are to be taken, then the user has the option to shut the system down, at step 106. Referring now to FIGS. 4A and 4B, if measurements are to proceed, the operator begins running the previously programmed test sequences. If the automatic mode was selected, the stored sequence of defined positions is sequentially carried out for automatically positioning the sensing head and DUT in the desired measuring orientations.

A test sequence generally involves first driving the DUT with an expected pattern, at step 108, such as a checkerboard design. The software, preprogrammed during the recording test sequence step, then positions the sensing head, at step 110, for the first measurement orientation. This involves sending appropriate commands to the respective linear and rotary controllers to drive the respective microstepping servos and generate positional movement along each axis with respect to the previously defined home positions.

With the sensing head in place, the software directs the instrumentation to acquire data, at step 112, with respect to the previously selected parameters such as luminance, chromaticity, contrast, correlated color temperature, spectral power distribution, viewing angle performance, and uniformity. The sensing head transmits the detected data to the computer, at step 114, and recorded to the memory, at step 116. The detected data may take the form of a serial data stream, or graphical input information. Once the data has been recorded, the sequencing iteratively proceeds to the next measurement position, at step 110, until the sequenced is finished, at step 118.

For the manual mode of operation, the software does not instruct the stages to change positions. Instead, the operator remotely controls any variations in positioning, for example, by controlling a joystick or other control mechanism to effect stage movement.

Once the sequence of measurements is finished, the test results are displayed to the operator, at step 120. To confirm the actual footprint followed by the cooperative action of the five stages, the measurement locations are displayed, at step 122. The software menu displays are then re-set, at step 124, and the measured data recorded to memory, at step 126.

The serial number or other identifying indicia of the DUT 12 may be entered as part of the measurement results to maintain traceability of the test data and the unit. If the test results fall within predetermined thresholds of acceptability, such as manufacturer's or customer's performance specifications or standards such as those defined by the International Standards Organization (ISO), then the DUT is acknowledged as a saleable unit. If the test results indicate a failure, then diagnostic routines may be performed as is well known in the art to determine the cause of the failure and indicate if rework or repair is possible.

Those skilled in the art will appreciate the many benefits and advantages offered by the system and method of the present invention. Of significant importance is the controllable footprint realized by the cooperation of the three-axes assigned to the instrumentation and the two rotary axes carrying the DUT. In this manner, measurement accuracy is substantially improved while allowing the capability for open ended architectural modifications and additions. A further advantage to having the instrumentation and the DUT movable as two separate entities involves the increased range of relative motion between the DUT and the sensing head.

While the invention has been particularly shown and described with reference to the preferred embodiments thereof, it will be understood by those skilled in the art that various changes in form and detail may be made therein without departing from the spirit and scope of the invention.

What is claimed is:

1. A system for inspecting an image-producing display according to a predetermined footprint, said system including:

a platform for supporting said display, said platform fixed to a first multi-axis positioning unit;

a sensing head disposed in confronting relationship with said platform to detect radiation emitted by said display, said sensing head carried by a second multi-axis positioning unit; and a controller having outputs coupled to said respective first and second positioners and operative to generate control signals for manipulating said respective positioners to arrange said display and said sensing head into one or more relative orientations defining said inspection footprint.

2. A system for inspecting an image-producing display according to claim 1 wherein:

said platform comprises a universal mount.

3. A system for inspecting an image-producing display according to claim 2 wherein:

said universal mount includes an open ended box-shaped bracket and a moveable face panel selectively adjustable along said bracket, said bracket and panel formed with a plurality of spaced-apart openings adapted to receive fastening elements to mount said display.

4. A system for inspecting an image-producing display according to claim 1 wherein:

said first multi-axis positioning unit comprises a goniometer.

5. A system for inspecting an image-producing display according to claim 4 wherein:

said goniometer includes two rotational axes disposed in orthogonal relationship to effect a north polar orientation.

6. A system for inspecting an image-producing display according to claim 1 wherein:

said sensing head includes a photometer.

7. A system for inspecting an image-producing display according to claim 1 wherein:

said sensing head includes a spectroradiometer.

8. A system for inspecting an image-producing display according to claim 1 wherein:

said sensing head includes a photometer and a spectroradiometer.

9. A system for inspecting an image-producing display according to claim 1 wherein:
said second multi-axis positioning unit comprises a plurality of linear stages.

10. A system for inspecting an image-producing display according to claim 9 wherein:
said linear stages are disposed in three orthogonal axes to define a Cartesian coordinate system.

11. A system for inspecting an image-producing display according to claim 1 wherein:
said controller includes multiple modes of operation.

12. A system for inspecting an image-producing display according to claim 11 wherein:
said controller includes automatic and manual modes.

13. A system for inspecting an image-producing display according to claim 1 wherein:
said controller includes a computer having memory.

14. A system for inspecting an image-producing display according to claim 13 wherein:
said computer includes software stored in said memory to define a displayable user interface.

15. A five-axis inspection system for measuring radiation emitted from flat panel displays, said system including:
a platform for supporting said display, said platform fixed to a north polar goniometer having two rotatable axes;
a sensing head disposed in confronting relationship with said platform to detect light produced by said display, said sensing head including a photometer and a spectroradiometer and carried by three linear stages disposed in orthogonal relationship and defining a Cartesian coordinate system; and
a computer driven controller having outputs coupled to said respective linear and rotary stages and operative to generate control signals for manipulating said respective stages and arranging said display and said sensing head into one or more relative orientations defining an inspection footprint.

16. A method of inspecting an image-producing display, said method including the steps of:
mounting said display on a first multi-axis positioning unit;
selecting a sensing head for measuring light generated by said display, said sensing head carried by a second multi-axis positioning unit disposed in confronting relationship with said display;
defining a footprint comprising a plurality of measurement orientations along a predetermined path; and
manipulating said respective first and second positioning units according to said defined footprint to cooperatively bring said display and sensing head into said plurality of measurement orientations and minimize positional accuracy therebetween.

* * * * *